(12) United States Patent
Weiss et al.

(10) Patent No.: US 7,386,161 B2
(45) Date of Patent: Jun. 10, 2008

(54) METHOD AND APPARATUS FOR FLAT PATTERNED MEDIA INSPECTION

(75) Inventors: Adam Weiss, Pickering (CA); Afsar Saranli, Toronto (CA)

(73) Assignee: Photon Dynamics, Inc., San Jose, CA (US)

( * ) Notice: Subject to any disclaimer, the term of this patent is extended or adjusted under 35 U.S.C. 154(b) by 561 days.

(21) Appl. No.: 10/688,326

(22) Filed: Oct. 17, 2003

(65) Prior Publication Data

US 2004/0109598 A1 Jun. 10, 2004

Related U.S. Application Data

(63) Continuation of application No. 10/439,991, filed on May 16, 2003.

(60) Provisional application No. 60/423,008, filed on Nov. 1, 2002.

(51) Int. Cl.
*G06K 9/00* (2006.01)

(52) U.S. Cl. ....................................... 382/141

(58) Field of Classification Search ..................... None
See application file for complete search history.

(56) References Cited

U.S. PATENT DOCUMENTS

| | | | |
|---|---|---|---|
| 4,579,455 A | 4/1986 | Levy et al. | |
| 4,589,140 A * | 5/1986 | Bishop et al. | 382/148 |
| 4,805,123 A | 2/1989 | Specht et al. | |
| 5,699,447 A | 12/1997 | Alumot et al. | |
| 5,907,628 A | 5/1999 | Yolles et al. | |
| 5,991,688 A * | 11/1999 | Fukushima et al. | 701/209 |
| 5,999,642 A * | 12/1999 | Gilliland | 382/154 |
| 6,519,357 B2 * | 2/2003 | Takeuchi | 382/149 |
| 6,674,889 B1 * | 1/2004 | Takayama | 382/149 |
| 6,870,169 B2 * | 3/2005 | Obara et al. | 250/492.2 |
| 2003/0118245 A1 * | 6/2003 | Yaroslavsky et al. | 382/255 |

* cited by examiner

*Primary Examiner*—Matthew C. Bella
*Assistant Examiner*—Alex Liew
(74) *Attorney, Agent, or Firm*—Townsend and Townsend and Crew LLP

(57) ABSTRACT

A concurrent low resolution/high resolution parallel scanning system and method are provided as an improvement in the scanning process of an inspection system for planar objects, such as large flat plates employed in panel displays, whereby lower resolution defect detection efficiently overlaps and parallels higher resolution defect review and classification stages in which defects are automatically defined and resolved. Although the invention is a valid solution for the more general problem of optically inspecting the surface of a flat article for defects, the invention is particularly useful for detecting pattern defects on large glass plates deposited with integrated-circuits for forming LCD flat panel displays.

6 Claims, 5 Drawing Sheets

METHOD AND APPARATUS FOR FLAT PATTERNED MEDIA INSPECTION

CROSS-REFERENCES TO RELATED APPLICATIONS

The present application is a continuation of U.S. patent application Ser. No. 10/439,991 filed May 16, 2003 which claims benefit of the filing date of U.S. provisional application No. 60/423,008 filed on Nov. 1, 2002, the entire content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

The invention relates to the general field of machine vision based inspection technology and more particularly to machine vision based detection and classification of defects occurring on large flat patterned surfaces. In particular, the invention addresses the inspection of materials deposited on large substrate glass plates such as Liquid Crystal Display (LCD) panels. Although the invention applies to the general case of the inspection of any flat patterned media, the invention is particularly related to the inspection of glass substrates used for Thin Film Transistor (TFT) LCD panels in precompletion form.

During the manufacturing of LCD panels, large clear sheets of thin glass are used as a substrate for the deposition of various layers of materials to form electronic circuits that will function as a multitude of identical display panels. This deposition is usually done in stages wherein, at each stage, a particular material, such as metal, Indium Tin Oxide (ITO), silicon, or amorphous silicon, is deposited over a previous layer (or upon the glass substrate) in adherence to a predetermined pattern often determined by a mask. Each process stage includes various steps such as deposition, masking, etching and stripping.

During each of the process stages and at various steps within a stage, various production defects may be introduced that affect the structure and that have electronic and/or visual implications on the final LCD panel product. Such defects include but are not limited to circuit shorts, opens, foreign particles, mask problems, feature size problems, over etching and under etching. In order for the final LCD panel to operate properly, these defects need to be detected, classified and if possible repaired, preferably at the stage they are generated. The decision to repair is based on accurate classification of defects and especially to the separation between "killer", "repairable" and "process" defects.

The operating resolution of the system for automatic defect detection often has a direct impact on the inspection speed and the cost of the system. Therefore, only comparatively lower resolutions are feasible to scan the entire area of the plate. Unfortunately, at this lower resolution it has not been possible in the past to simultaneously perform both detection and reliable classification from the same image data collected. Also, low resolution has an impact on the performance of the detection algorithms, which often result in a substantial number of false alarms which need to be eliminated. Therefore, following a defect detection step, there is a need for a defect review step, wherein a higher resolution inspection (via camera) is used to capture the defect area of interest for subsequent validation of the defect candidate and thereafter to perform either automatic or human assisted classification.

In this type of operation, a low resolution sub-system is used to detect the problem areas of the plate (Defect Detection Sub-System—DDS) while a separate high resolution camera is used at a later stage to capture high resolution images for these problem areas (Defect Review Sub-System—DRS) for the purpose of higher reliability automatic or manual classification. As long as the number of problem areas detected by the DDS can be kept within manageable limits, high resolution image capture for these singular points remains feasible. Still, this number has often a direct impact on either the cycle time of the system (if all defects are to be reviewed) or on the review performance of the system (if a fixed limited number of defects are reviewed).

Automated Optical Inspection (AOI) equipment has been used for a variety of problems including but not limited to Printed Circuit Board (PCB) inspection, silicon Very Large Scale Integrated (VLSI) circuit wafer (die) inspection, as well as LCD panel inspection. Most of the implemented solutions are based on spatial domain pattern comparison techniques often used in combination with sensor level pixel or sub-pixel precision alignment techniques.

U.S. Pat. No. 4,579,455 to Levy et al. describes an alignment and pattern comparison technique where a pair of 7×7 windows are considered on the test and reference images and squared sum of errors over a multitude of possible 3×3 sub-windows within this window are computed. If the minimum error over these combinations exceeds a threshold value, a defect is assumed. The method appears to be capable of compensating for alignment mismatch down to a sensor pixel level.

Addressing issues about the coarse alignment precision of the method by Levy et al., U.S. Pat. No. 4,805,123 to Specht et al. describes an improved alignment and comparison technique for the detection of defects. In this technique, large windows in test and reference images are used to compute a sensor pixel level correlation between test and reference. The resulting sampled correlation surface's minimum point is found and a quadratic function is fitted to the surface in the neighborhood of this minimum point. Using the fitted quadratic function, a sub-pixel precision translation is obtained to align the test and reference images. The aligned images are compared by thresholding image differences on 2×2 sub-windows on the test and aligned reference images.

Variations and improvements on these basic techniques have also been proposed such as U.S. Pat. No. 5,907,628 to Yolles et al., which among other things point out to the drawbacks of using the sampled correlation surface to find the minimum and argue that due to coarse sampling of the surface this point may not correspond to the true minimum. Hence, they argue that the subsequent sub-pixel interpolation step would do little to improve the detected minimum and a false alignment would result, leading to false alarms in detection. Yolles et al. proposes to alleviate these problems by an elaborate comparison process based on improved comparison entities.

With any of the above methods, the use of a single feasible (comparatively low) resolution for scanning the entire surface of the article inspected leads to a set of defect candidates. These defect candidates necessarily include both legitimate defects as well as false alarms, due to the inability of the methods to completely filter out expected variations between a test and reference image. This results in the alarm to be a set of defect candidates and arises the need to validate the candidates to form the true defect map of the article inspected. Furthermore, there is a strong need to classify the legitimate defects into a number of defect classes to help with the disposition of the article inspected, in some applications possibly enabling the article to be repaired.

One solution along these lines has been proposed by U.S. Pat. No. 5,699,447 to Alumot et al. which describes a two stage scanning approach. The entire panel is first scanned at a higher speed by a stage of a comparatively low resolution non-Charge Coupled Device (CCD) optical system with a small diameter laser beam in a raster scan mode. This is followed by a second stage scan with a high resolution CCD-based optical system. The latter scanning stage extracts the higher resolution images of all the defect suspect locations which have been detected by the former scanning stage. Although this solution addresses the need to extract higher resolution images of the detected objects for their validation, it is different from the current invention in that the first stage of examination is by means of a raster scan with a small diameter laser beam and also for the fact that the two examinations are in sequential stages. The disadvantages include the following:

(a) Increased cycle time: The high resolution imaging stage comes immediately after the main detection stage. The sequential nature of the high resolution imaging has considerable impact on the inspection cycle time since the time required for high resolution image acquisition, review and classification is added to the time required for the detection scan.

(b) Idle imaging resources: The high resolution defect review imager is idle while the detection imager is active and the detection imager is idle while the review imager is active. This leads to an inefficient use of the system resources within the given time constraints.

(c) Non-optimal review process: When classification is necessary, and production environment time constraints prevent the imaging of all candidate locations, the user of the system may be left with the difficult task of deciding how many and which of the candidates to collect and process with the high resolution review imager.

What is needed is a fully automatic and overlapped high resolution defect review system operating in combination with a rapid and accurate classification technique to improve both the speed and accuracy of inspection and repair.

SUMMARY OF THE INVENTION

According to the invention, a concurrent low resolution/high resolution parallel scanning system is provided as an improvement in the scanning process of an inspection system, whereby a lower resolution defect detection stage efficiently overlaps and parallels higher resolution defect review and classification stages in which defects are automatically defined and resolved. Although the invention is a valid solution for the more general problem of optically inspecting the surface of a flat article for defects, the invention is particularly useful for detecting pattern defects on large glass plates deposited with integrated-circuit LCD panels. Therefore, the invention will be described in relation to this particular application.

The invention provides an improved system which is mechanically and electronically capable of performing a low resolution and a high resolution imaging of the surface of the subject of inspection concurrently in time. This includes two independent and parallel imaging sub-systems of different resolutions, each capable of acquiring images in parallel from the surface of the article to be inspected. The low resolution imaging stage includes a Defect Detection Sub-System (DDS) and the high resolution imaging stage includes a Defect Review Sub-System (DRS). Furthermore, each of these sub-systems may in turn have one or more imaging channels.

The DDS covers the entire surface subject to inspection, using typically a number of identical, comparatively lower resolution imaging optics and optical-to-electrical converters (such as CCD devices or Complementary Metal Oxide Semiconductor (CMOS) photo-sensitive devices). The explicit purpose of this sub-system is to distinguish defect candidates and optionally to pre-classify them based on the defect location relative to the TFT lattice features. Such pre-classification may categorize defect candidates as related to: data line, gate line, transistor, capacitor and ITO electrode. Since the number of defects which can be reviewed in a given time is limited, the defect pre-classification results could be used for prioritizing defects competing for review. The defect-candidates prioritization is accomplished by assigning to each candidate a review worthiness factor corresponding to the result of pre-classification.

The DDS may be mounted on a moving apparatus which travels along the subject to be inspected, possibly performing a plurality of passes or alternatively, it may be fixedly mounted over a moving surface carrying the article to be inspected.

The DRS covers a substantially smaller area subject to inspection, using a small number of identical, comparatively higher resolution imaging optics and optical-to-electrical converters. The specific aim of this sub-system is to image, with high resolution, the defect candidates identified and pre-classified by the DDS subsystem to facilitate automatic final defect classification. The DRS imaging channels can be mounted on a moving apparatus which travel along the subject to be inspected in synchrony with the DDS. Each DRS channel further can move independently across the subject to be inspected.

By means of overlapping the low resolution defect detection and high resolution defect review and classification functionality, the present invention seeks to significantly reduce overall cycle time for the automatic optical inspection of flat, large, patterned articles. Applied to the TFT LCD inspection problem considered, this increases the value of the (Automated Optical Inspection Instrument) AOI instrument for the users which are usually operating under tight cycle-time constraints hence increase the chance of an AOI system being used for in-line 100% TFT-LCD plate inspection.

The inspection is facilitated through mechanical motion of the DRS imaging channels coordinated dynamically by means of a dispatching algorithm. This algorithm seeks to optimize the defect review effort by maximizing the number of high priority defect candidates captured by the DRS while minimizing the distance traveled by the sub-system modules. The inputs to this algorithm are the spatial distribution of the defect candidates detected by the DDS in the plane of the glass plate and the review worthiness factors assigned to the defect candidates by the DDS. The result of the dispatching algorithm is the optimal motion pattern for each individual DRS module. This motion pattern is then executed by the DRS motion system.

The optimal dispatching algorithm hence minimizes the number of defect candidates which cannot be reviewed with high resolution imaging of the DRS with a given number of camera modules. It also enables the priority capture of those defect candidates which are more important for high resolution imaging. Overall, this either results in the minimization of the number of camera modules required for a given defect candidate distribution, potentially reducing the system cost figure, or it improves the performance of the system with the same number of camera modules.

One particular embodiment of the dispatching algorithm can be based on Graph Theory and will be detailed for illustrative purposes in the present disclosure. However, other alternative implementations of the dispatching algorithm are possible and the invention is not limited to the particular details of the algorithm depicted.

On-the-fly (OTF) focusing is typically a required feature of the present invention to realize the overlapped concurrent DDS/DRS system with low and high resolution by bringing the high resolution imaging system into sharp focus at the candidate defect locations. It increases the time efficiency of the overall scheme and enables the DRS to operate without stopping along the y-axis.

The real-time concurrent review and classification which is a part of the DRS minimizes the need for human intervention in the inspection process and increases the cycle time efficiency of the system.

The present invention and its components act as a pipeline of inspection and associated processing, keeping all critical stages of the inspection fully active and utilized during the scan of the article being inspected.

The invention will be better understood by reference to the following detailed description in connection with the accompanying drawings.

DETAILED DESCRIPTION OF SPECIFIC EMBODIMENTS

Figure 1:
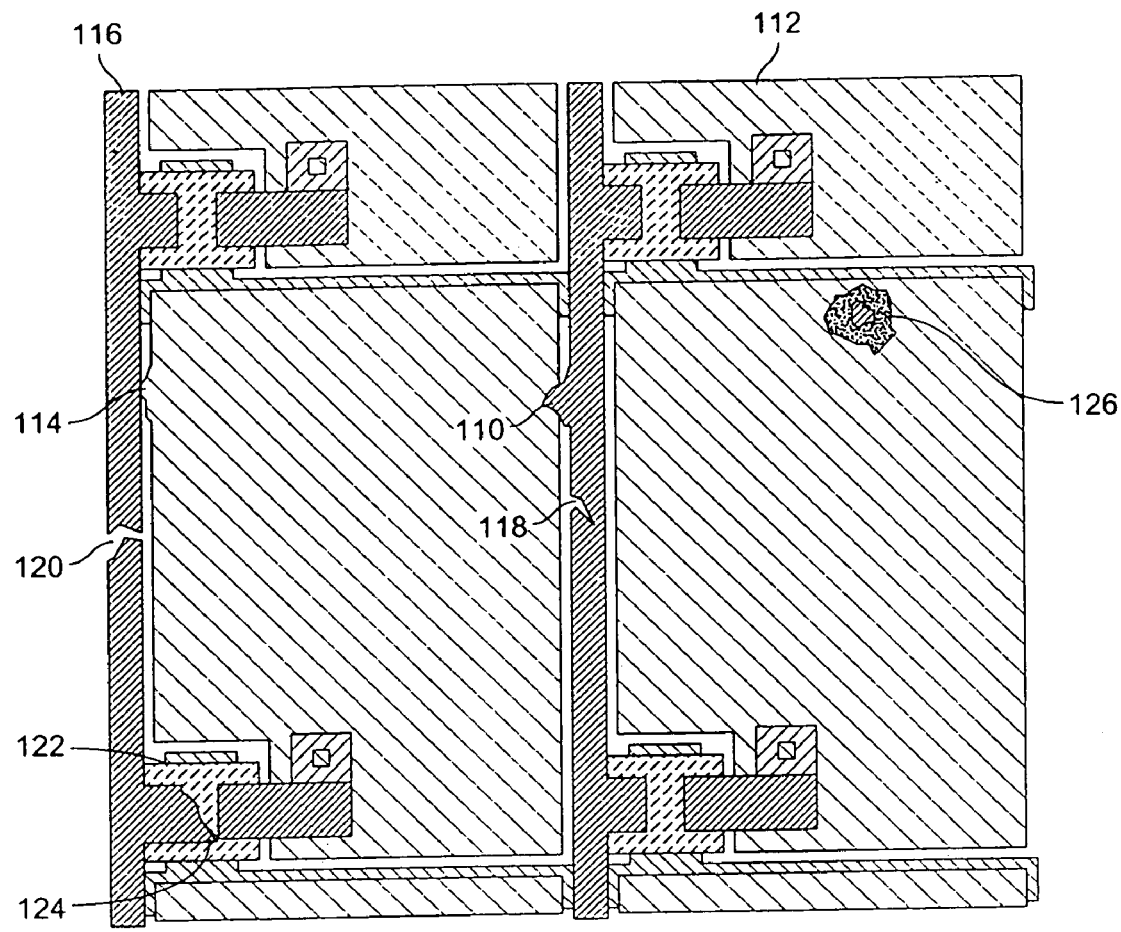
FIG. 1 is a top view of a small region of a panel portion illustrating possible defect types.

Referring to FIG. 1, there is an illustration of some of the possible defects that can be found during the manufacturing process for LCD panels. These include a metal protrusion 110 into an ITO layer 112, an ITO protrusion 114 into metal 116, a so-called mouse bite crack 118 in metal 112, an open circuit 120 in metal 116, a transistor short 124 in the transistor 122 of a pixel, and a foreign particle 126 in any region. Each of these types of defects must be detected, classified and if possible repaired.

According to the invention, an inspection platform 10 (FIG. 2A or 2B) is provided with a Defect Review Sub-System (DRS) 12 which comprises a plurality of substantially identical, comparatively higher resolution imaging optics and optical-to-electrical converters together forming a set of camera modules 14, 16, 18 that are capable of moving together, as on a gantry 20 along the length of the article to be inspected 22 in coordination with scanning motion of a Defect Detection Sub-system (DDS) 24. Each identical camera 14, 16, 18 is further capable of independently moving across the scanning motion of the Defect Detection sub-system 24.

Figure 2A:
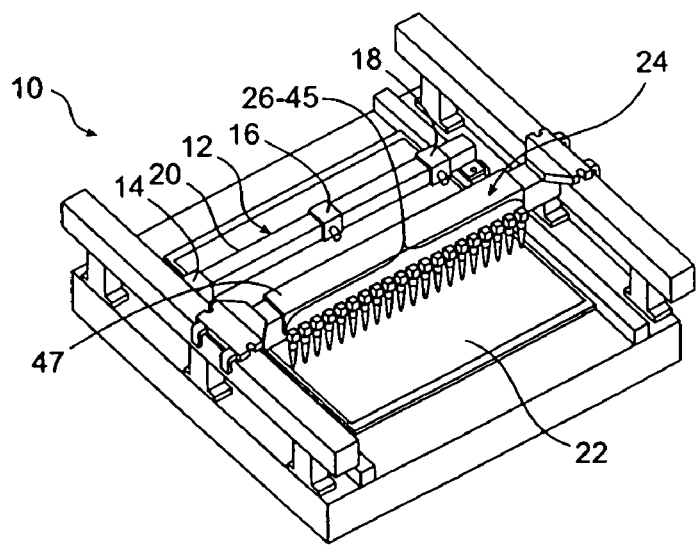
FIG. 2A and FIG. 2B are perspective views from different perspectives of one possible implementation of the invention corresponding to opposing scanning directions.
Figure 2B:
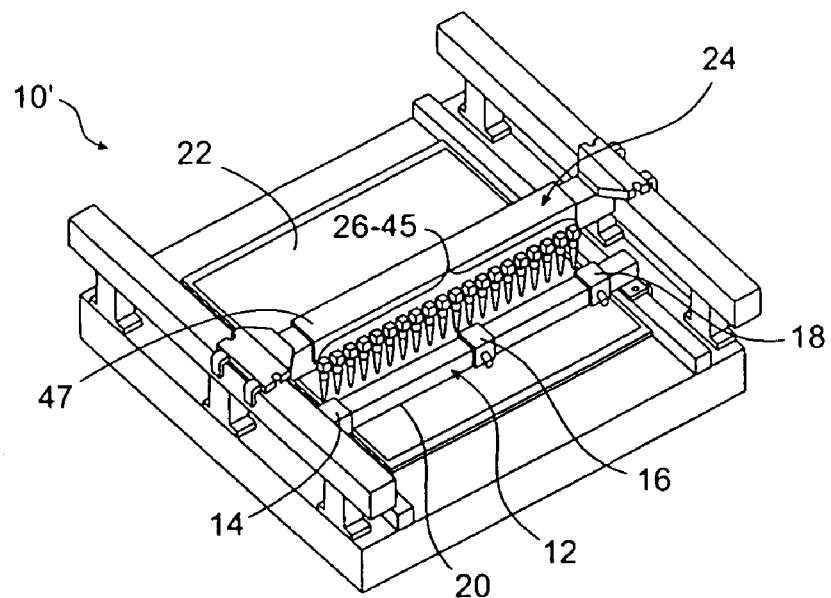

One suitable mechanical layout of such a system is presented in FIGS. 2A and 2B for two opposite directions of scan where the DRS 12 is placed on its own scanning gantry 20 capable of moving along the direction of the low resolution scan. Individual high resolution DRS modules 14, 16, 18 are operative to move across the main scanning direction. Twenty DDS 24 modules 26-45 and the three DRS modules 14, 16, 18 are displayed for illustration purposes. The actual numbers of modules may be determined by the needs of the particular application. The DRS modules 14, 16, 18 need not necessarily be on a separate gantry 20, but they may as well be mounted on the same gantry such as the DDS gantry 47. Also, a scan using a linearly actuated gantry, although being illustrated here, is not the only method considered for performing the imaging scan over the surface of inspection. Alternative methods of performing this scan, such as a tilt rotating mirror scanner with appropriately designed stationary optics, are possible, and the algorithms disclosed herein can be adapted accordingly.

The operation of the DDS/DRS concurrent system 10 comprises causing the lower resolution DDS 24 on gantry 47 to scan over the entire area of the subject to be inspected, possibly in multiple passes, where each pass covers a percentage of the total area. During each such pass, the DDS 24 performs basic defect detection and classification where lists of defects and defect candidates are generated. These defect candidates are then queued for dynamic dispatching to be imaged by the DRS 12 at a comparatively higher resolution.

Each such defect candidate is further associated with a DRS worthiness measure to indicate the importance level of imaging this particular candidate with high resolution. The DRS 12 which follows the DDS 24 with a coordinated motion performs an optimal motion pattern to maximize the number and worthiness of defect candidates which can be captured at that pass. The candidates which could not be captured at the current pass are scheduled for the subsequent passes. The details of this process are set forth in the following sections.

Slight changes in the flatness of a large article to be inspected over the scanning area combined with the very small depth-of-field of the typical optics of the DRS modules 14, 16, 18 necessitates a dynamic focusing scheme for the DRS modules. Hence, the present invention incorporates DRS modules 14, 16, 18 which are capable of performing dynamic auto-focusing during travel to the candidate defect location. This feature is detailed in the following sections.

DRS Module Dispatching

One feature of the present invention is a process to dispatch the available high resolution DRS modules 14, 16, 18 to the scheduled defect candidates so as to optimize the effort spent for defect review by maximizing the number and DRS worthiness of the captured defect candidates while minimizing the distance traveled by the modules. One particular embodiment of such a dispatching algorithm is based on Graph Theory and will be described here for illustrative purposes. The invention is not limited with the specific details of the algorithm and alternative methods of providing the dynamic dispatching can be used.

Based on the assumption that expected defect distribution is uniform, each DRS module 14, 16, 18 is considered autonomous with a minimum amount of interaction needed to account for x-span partitioning of responsibilities and collision prevention, as described below.

As the DDS 24 scans, it reveals the defect candidates which are to be concurrently imaged by one of the high resolution DRS modules 14, 16, 18. Due to the mechanical acceleration and speed constraints on the design of the system, the DRS modules 14, 16, 18 that follow them may not be able to capture all the revealed defect candidates on the same pass. The full details of a specific dispatching algorithm are not given in this disclosure, but a list of critical procedures is given and some of the critical constraints that must be considered are outlined here so that one of ordinary skill in the art may formulate a suitable dispatching algorithm. The dispatching algorithm for dispatching the selected DRS modules 14, 16, 18 to the defect candidates takes into account the mechanical constraints on module motion, such as maximum acceleration and speed, the requirements for dynamic focusing, the number of defects that can be captured by alternative motion patterns, and the value or DRS worthiness of individual defects. A suitable dispatching algorithm also deals with the presence of multiple passes over the scan area, effectively enabling defect candidates which could not be captured on the current pass to be captured on the subsequent passes.

The DRS module dispatching process should consider a fixed or variable look-ahead window in the main direction of scanning (denoted as y-axis in the x-y plane) to determine the dynamic list defect candidates subject to dispatch optimization of DRS imaging modules. Alternatively, this window may cover the whole glass span in which case all pending defect candidates are considered for this dispatch optimization. For any given distance along the y-axis, an individual DRS module has a feasible Field Of Access (FOA) of an area within which any point is reachable by the module, assuming that the module is initially stationary and is again intended to be stationary at the end of the motion. This is the feasible field of access illustrated in FIGS. 3A and 3B.

Figure 3A:
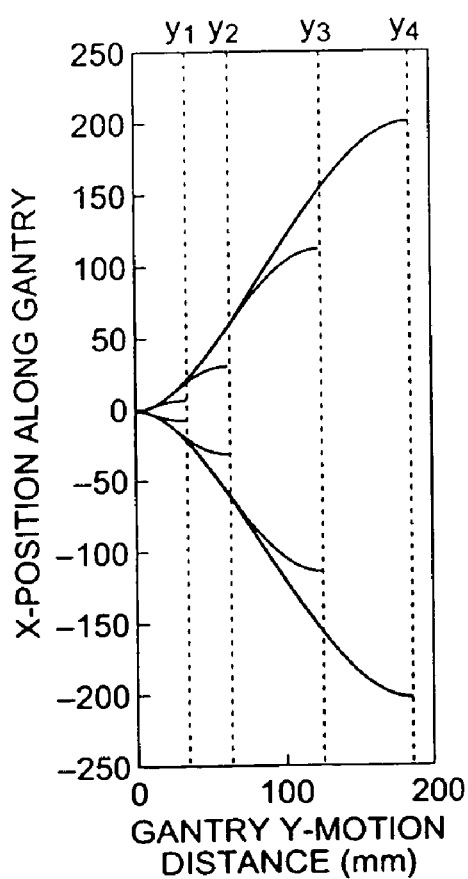
FIG. 3A and FIG. 3B are graphs of feasibility boundaries.
Figure 3B:
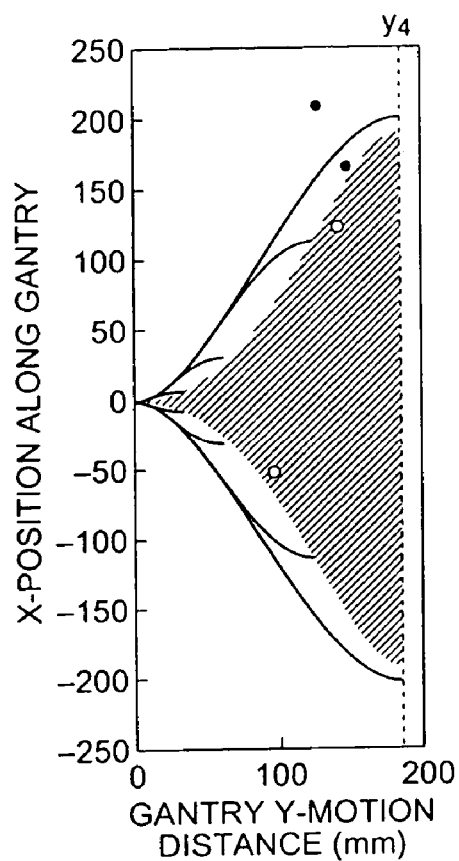

As illustrated in FIGS. 3A and 3B, each initial position and velocity for a particular DRS module and a pre-selected look-ahead window on the y-axis leads to a specific feasible field of access. This field of access region determines which defects are reachable from the current location of the DRS module. However, once the module starts moving towards a target location, possibly a candidate defect, this area changes and must be recomputed. The shape of this area changes if the module is not x-axis stationary when the area is computed.

According to the particular embodiment of dispatching algorithm illustrative here, through the feasible field of access computation, the DRS modules of the present invention each process the candidate defect map visible in the chosen y-axis window to perform the following steps:

(a) Constructing a forward flow graph with nodes corresponding to defects candidates and the present module position, and arcs corresponding to feasible motions from the current position to defect candidates and in between the defect candidates;

(b) For each arc signifying a module movement from one defect candidate to another defect candidate, a cost factor is computed. The cost factor comprises the physical candidate-to-candidate distance value, the penalty for missing other defects (due to the new feasible field of access resulting at the new location) and the negative cost (or benefit—determined by its review worthiness) of capturing the target defect;

(c) Solving the resulting graph for the minimum cost path from the current location to the end of the y-axis window considered; and (d) Computing the necessary motion trajectory for the corresponding DRS module.

Figure 4A:
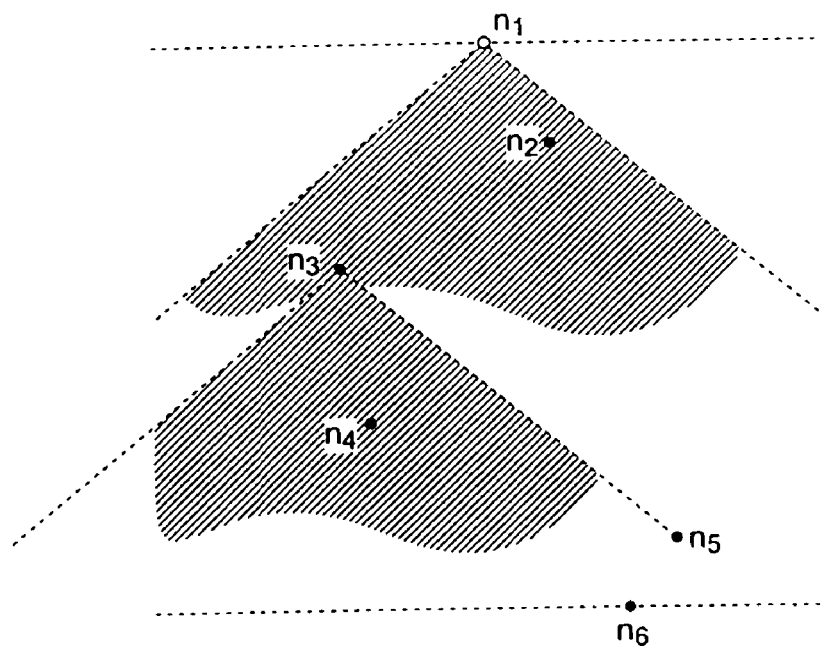
FIG. 4A, FIG. 4B and FIG. 4C are graphs to illustrate access strategies.
Figure 4B:
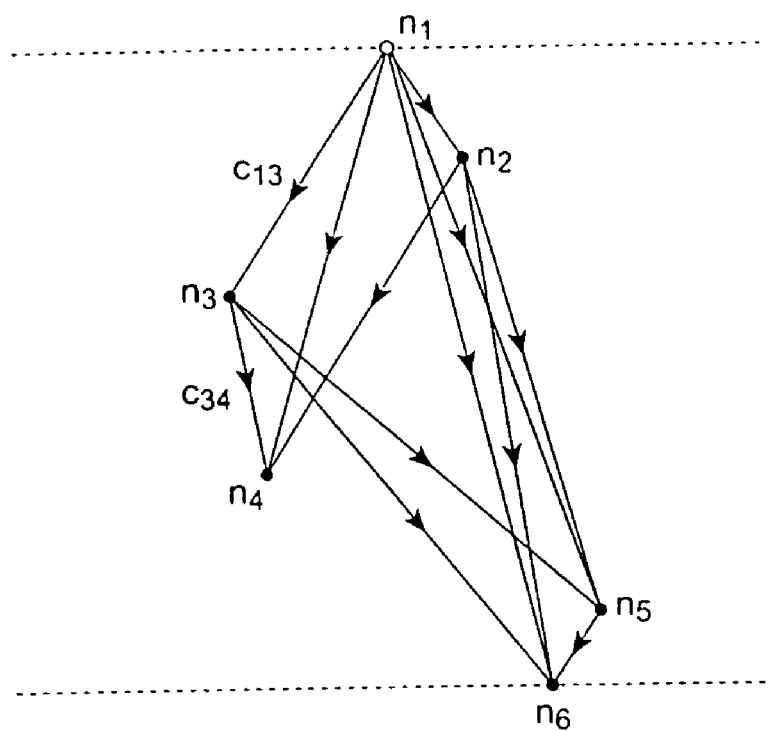
Figure 4C:
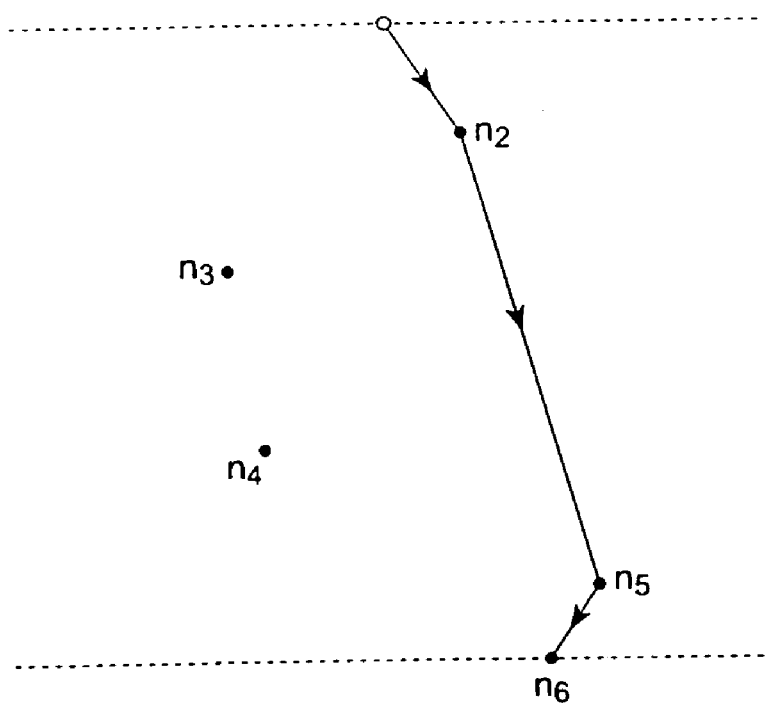

FIGS. 4A through 4C illustrate the foregoing process. As long as the set of defect candidates falling within the considered y-axis look-ahead window do not change, the motion solution will be optimal. However, as soon as new defects, possibly with different worthiness values, come into view of the window, the current motion solution may no longer be optimum, and the above procedure should be repeated to find a new optimum path for the subject DRS module. The subject module may already be in motion towards a defect when the new solution is computed. Depending on the new optimum solution, the module may change direction to target a different candidate location.

As a feature of the present invention, arc costs are determined as a suitable function of the negative cost (i.e., benefit) of capturing the target defect candidate, the cost of defect candidates missed when this arc is selected and the total distance and energy costs of the movement associated with the arc. Individual factors in the total cost are normalized to compatible dynamic ranges and are weighted according to the requirements of the particular application to generate the final arc cost.

The resulting "shortest path finding" Graph Theory problem is solved for the minimum cost path from the current module location up to and including the last defect candidate location along the y-axis within that module's look-ahead window. After capturing the last defect candidate in computed sequence, the module then remains x-stationary until another new defect candidate appears within the look-ahead window in which case the process is repeated. The solution to the Graph Theory problem is generated by making use of one of the well-established algorithms in this field. For example, Dijkstra's Algorithm known to the art for shortest path or an incremental variant thereof seem well suited for the task, but other alternatives may also be considered.

A further feature of the present invention is the incorporation of boundary conditions and the presence of adjacent modules into the formulated graph by means of additional limits on the feasible fields of access. The adjacent DRS modules across the same x-axis are each assigned a zone of dispatch of equal size and with an appropriate amount of overlap between them. This partition of the x-span into equal sized zones is based on the assumption of uniform defect distribution.

It is possible for a defect candidate to fall into the overlap zone between two adjacent DRS modules, in which case it will be taken into account in the solution of both of the modules. This case does not lead to any collision conditions if only one or none of the modules have included that particular defect in their optimal dispatch trajectories. In case both optimal paths have included that particular defect, the algorithm is optioned to consider the computed total optimal solution costs for the two modules and to assign the defect to the module leading to the minimum of the two total optimal costs. For example, where, $m_i$ and $m_{i+1}$ are the two adjacent modules and $C^*_i$ and $C^*_{i+1}$ are the two optimal solution costs, the defect is assigned to module k which satisfies:

$$k = \arg\min\{C_i^*, C_{i+1}^*\} \quad (1)$$

Upon finding the optimal dispatching solutions for all of the DRS modules, the corresponding motion data is computed and sent to the DRS motion control hardware. This relationship holds for the various gantry combinations contemplated by the invention.

DRS Camera Module Dynamic Auto-Focusing

Another feature of the present invention is a process of dynamically adjusting the focus of the DRS camera modules and finding the optimal focus point. This is done while the module is in motion towards the target defect candidate location, as explained below.

There are random deviations from flatness throughout the span of a large flat article being inspected. These deviations are assumed to be of low spatial frequency (i.e., happening slowly along the x-y plane). This effect is combined with a very narrow depth of field of a very high microscopic magnification required for high resolution imaging. Therefore, for every new location imaged, the optics must be refocused. In order to maximize the defect coverage by the DRS modules, the focusing needs to be done on-the-fly, that is, while the module is traveling to the defect candidate location. This is especially required in embodiments where the DRS modules are mounted on the same gantry as the DDS, since the latter has a constant y-axis motion dictated by the requirements of the low resolution line-scan imaging.

In one embodiment, the present invention seeks to achieve optimal focus at the defect candidate location by performing a series of full or partial image captures during the travel towards the defect candidate. In any embodiment, the dynamic focus procedure is initiated and completed at a close enough distance to the target location so that the obtained focus point is valid on the target location.

The process works by means of the steps of:

(a) Capturing a sequence of image data from the DRS camera module beginning at a pre-determined distance away from the target candidate location, and during the motion of the module;

(b) Sampling the focus quality curve by using the sequence of image data extracted from the camera module in combination with a focus quality measure computed over these images;

(c) Interpolating the samples with a smoothing function to determine a maximizing focus point for the z-stage moving the focusing optics; and (d) Directing the z-actuator to the position maximizing the focus quality criterion to achieve the sharpest focus on the target area.

Figure 5A:
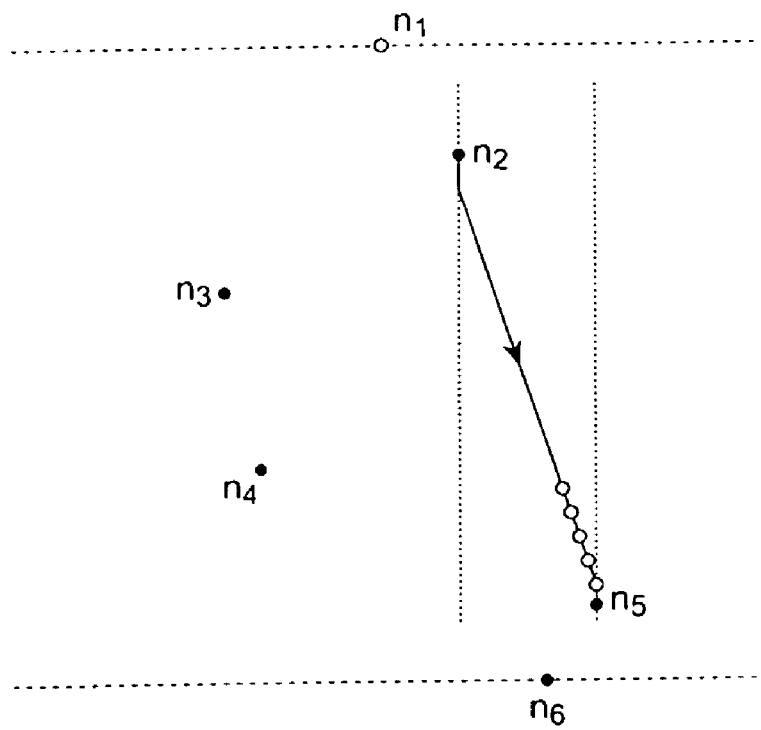
FIG. 5A and FIG. 5B are graphs to illustrate auto-focusing strategies.
Figure 5B:
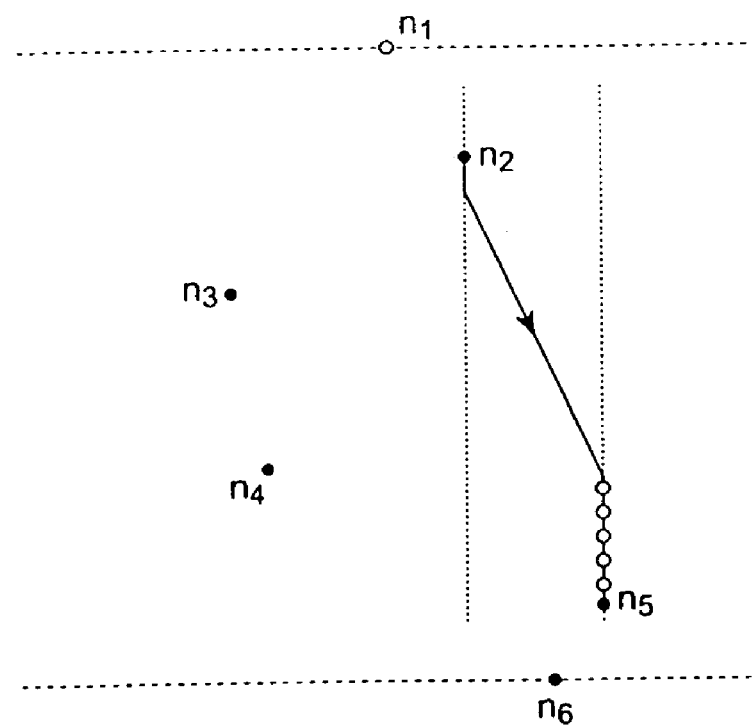

FIGS. 5A and 5B illustrate module motion from defect candidates $n_2$ to $n_5$ assuming that $n_5$ is still feasible under the additional constraint. Depending on the nature of the required optics, such as for a line scan sensor or an area scan sensor, needed for the application, the image capture steps in (a) may be effected either during an arbitrary diagonal motion of the module (moving also in x-axis direction) (FIG. 5A) or only when the camera becomes x-stationary (FIG. 5B). In the latter case, the feasible field of access computation takes into account the additional x-stationary period at the end of the motion for focusing purposes.

The focus quality measure used in step (b) may be based on image contrast as well as on the highest frequency content in the image as limited by the Modulation Transfer Function (MTF) of the lens system used.

DRS On-the-Fly Defect Candidate Classification

The system may perform concurrent review and automatic classification of the defect candidates found on the article being inspected by using the high resolution images collected by the DRS.

The DDS generates a stream of defect candidates which are queued and scheduled for imaging by a plurality of DRS modules. The DRS modules are dispatched to perform high resolution imaging of the outstanding defect candidates by means of the method described in the preceding sections. This results in a stream of defect candidates which are associated with high resolution image data. The defect candidates experience a two stage processing involving:

(a) Automatic Review; and
(b) Automatic Classification.

During the Automatic Review (AR) process, the high resolution candidate image is compared with a reference image (or more specifically data representative of a reference image) stored in system memory, that was captured previously either with the same module or with a different module. This step involves the compensation of known variations between the test and reference, including correcting for such things as camera sensitivities, sensor pixel sensitivity variations, and spatial misalignment at sensor pixel level. Due to the high resolution of the DRS modules, sub-pixel alignment is not necessary.

The result of the automatic review process is either the validation of the existence of a legitimate defect at the candidate location or the rejection of the defect as a "false" defect, i.e., an artifact of the known limitations of the low resolution DDS. The legitimate defects are forwarded to the Automatic Classification stage.

During the Automatic Classification (AC) stage, the high resolution defect image in combination with the output of the AR stage are used to extract the relevant features of the defect and make a final decision on the type of the defect through a classification process. The individual features which may be of interest depends on the particular application but would include defect size, defect location, defect shape and signal level.

In the case of the considered TFT-LCD plate inspection for production defects, the primary output of the classification system is to determine whether a defect is:

a) a process defect,
a repairable defect or
a killer defect.

Sub-categories within these main decisions are considered based on the requirements of a particular user.

A further feature of the present invention is the ability to realize the aforementioned stages in parallel, namely as concurrent processes. For example, the AR and AC stage operation is active concurrently as part of the DRS operation while the DDS is also performing the low resolution scan of the entire surface of the article being inspected.

The invention has been explained with reference to specific embodiments. Other embodiments will be evident to those of ordinary skill in the art. It is therefore not intended that this invention be limited, except as indicated by the appended claims.

What is claimed is:

1. A method for detection of defects, concurrent with on-the-fly review and classification of defect candidates in a flat patterned object under test comprising the following parallel operations:

acquiring images of the object;
detecting a first defect of said object;
assigning review worthiness values to said first defect through a defect detection sub-system having a plurality of defect detection sub-system modules operative according to a first relatively lower operating resolution;
detecting a second defect of said object and assigning review worthiness values to said second defect
acquiring images of smaller areas around said first defect reviewing said first defect, and classifying said first defect through a defect review sub-system having a plurality of defect review sub-system modules operative according to a second relatively higher resolution, wherein the detection of said second defect is performed concurrently with the review of the first defect;
maximizing a number of higher priority defect candidates captured by said defect review sub-system modules and minimizing distance traveled by said defect review sub-system modules using a dynamic defect review sub-system module dispatching algorithm for optimizing motion in said concurrent higher resolution reviewing, wherein said dispatching algorithm further comprises:
constructing, for each defect review sub-system and at each iteration of said motion optimization, a forward feasible motion graph in a Graph Theory sense with nodes corresponding to each defect candidate and current position of its associated module, and with arcs corresponding to feasible motions in between said nodes;
associating costs for each said arc signifying a module movement from the first defect to the second defect according to a suitable cost function selected from functions representing the cost of missing other defects, distance of required motion and review worthiness of a target defect candidate, and thereby obtaining a resulting graph;
solving the resulting graph for finding a minimum cost path, represented by an ordered sequence of defect to defect transitions, from the current location of the defect review sub-system module to the end of a window considered along scanning direction; and
computing motion data for the defect review sub-system module for controlling motion of the defect review sub-system module.

2. The method according to claim 1 further comprising:
beginning at a pre-determined distance from a target candidate location, and during the motion of the defect review sub-system module, automatically focusing the imaging element;
obtaining a focus quality metric curve using at least samples of a focus quality metric computed over the images;
interpolating the samples of the focus quality metric curve with a smoothing function to determine a maximizing focus point for a z-stage used for moving the focusing optics; and
directing the z-stage to the z-axis position which maximizes the said focus quality metric curve to achieve sharpest focus of the target candidate location.

3. The method according to claim 2 wherein said focusing step includes:
capturing a sequence of image data from an imaging element of the defect review sub-system; and wherein said obtaining step comprises
using a sequence of image data in combination with said focus quality measure computed over the images to sample the focus quality curve.

4. A method for detection of defects, concurrent with on-the-fly review and classification of defect candidates in a flat patterned object under test comprising the following parallel operations:
acquiring images of the object;
detecting a first defect of said object;
assigning review worthiness values to said first defect through a defect detection sub-system having a plurality of defect detection sub-system modules operative according to a first relatively lower operating resolution;
detecting a second defect of said object and assigning review worthiness values to said second defect
acquiring images of smaller areas around said first defect reviewing said first defect, and classifying said first defect through a defect review sub-system having a plurality of defect review sub-system modules operative according to a second relatively higher resolution, wherein the detection of said second defect is performed concurrently with the review of the first defect:
generating in the defect detection sub-system, a sequence of defect candidates;
queuing and scheduling the sequence for imaging by a plurality of the defect review sub-system modules;
dispatching the defect review sub-system modules to perform relatively higher resolution imaging of outstanding defect candidates to create a sequence of defect candidates associated with the relatively higher resolution image data;
causing the defect candidates to experience a two stage processing involving:
an automatic review process; and
an automatic classification process;
during the automatic review process, comparing the high resolution candidate image with a reference image stored in system memory of known defect status, wherein the comparing comprises compensating for known variations between test and reference including correcting for at least one of the following:
a) imaging instrument sensitivities, and
b) sensor pixel sensitivity variations;
compensating for spatial misalignment at sensor pixel level to result in either the validation of the existence of a legitimate defect at the candidate location or rejection of the defect as a false defect, including an artifact of known limitations of the low resolution DDS;
conveying information on legitimate defects to for automatic classification processing; thereafter
during automatic classification processing, using the relatively higher resolution defect image in combination with output of the automatic classification processing to extract relevant features of the defect; and
making a final decision on type of the defect through the classification processing.

5. An apparatus for defect detection, concurrent on-the-fly defect review and classification of phenomena in an object under test, said apparatus comprising:
a defect detection sub-system having a plurality of defect detection sub-system modules for acquiring images of the object, for detecting defect candidates and for assigning review worthiness values to said defect candidates according to a first relatively lower operating resolution; and a defect review sub-system having a plurality of defect review sub-system modules operative to acquire images of a smaller area around the defect candidates, for reviewing said defect candidates and for classifying said defect candidates as defects using a relatively higher resolution, wherein said defect review sub-system reviews a first one of said defect candidates while said defect detection subsystem detects a second one of said defect candidates, wherein the defect detection sub-system comprises a plurality of detection modules fixedly mounted on a first moveable gantry and the defect review sub-system comprises a plurality of defect review sub-system modules mounted for motion along on a second moveable gantry, said first and second moveable gantries adapted to move along a same direction, wherein motion of first ones of said review modules is limited by position of second ones of said review modules and further including a controller operative to:

construct a forward flow graph with nodes corresponding to defect candidates and current position of one of the defect review sub-system modules, and with arcs corresponding to feasible motions from the current position for the defect review sub-system module to first selected defect candidates and in between second selected defect candidates;

for each arc signifying a module move from one defect candidate to another defect candidate, associate costs to arcs as a function of cost factors, including a cost of missing other defects, distance of necessary motion, and worthiness of a captured defect to obtain a resulting graph;

solve the resulting graph for minimum cost path from the current location of the defect review sub-system module to an end of a y-axis window considered; and compute motion data for the defect review sub-system module for controlling motion of the defect review sub-system module.

6. The apparatus according to claim 5 wherein the defect detection sub-system is mounted on a first moveable gantry and the defect review sub-system is mounted on a second moveable gantry, said first and second moveable gantries adapted to move along a same direction.

* * * * *